Figure 1:
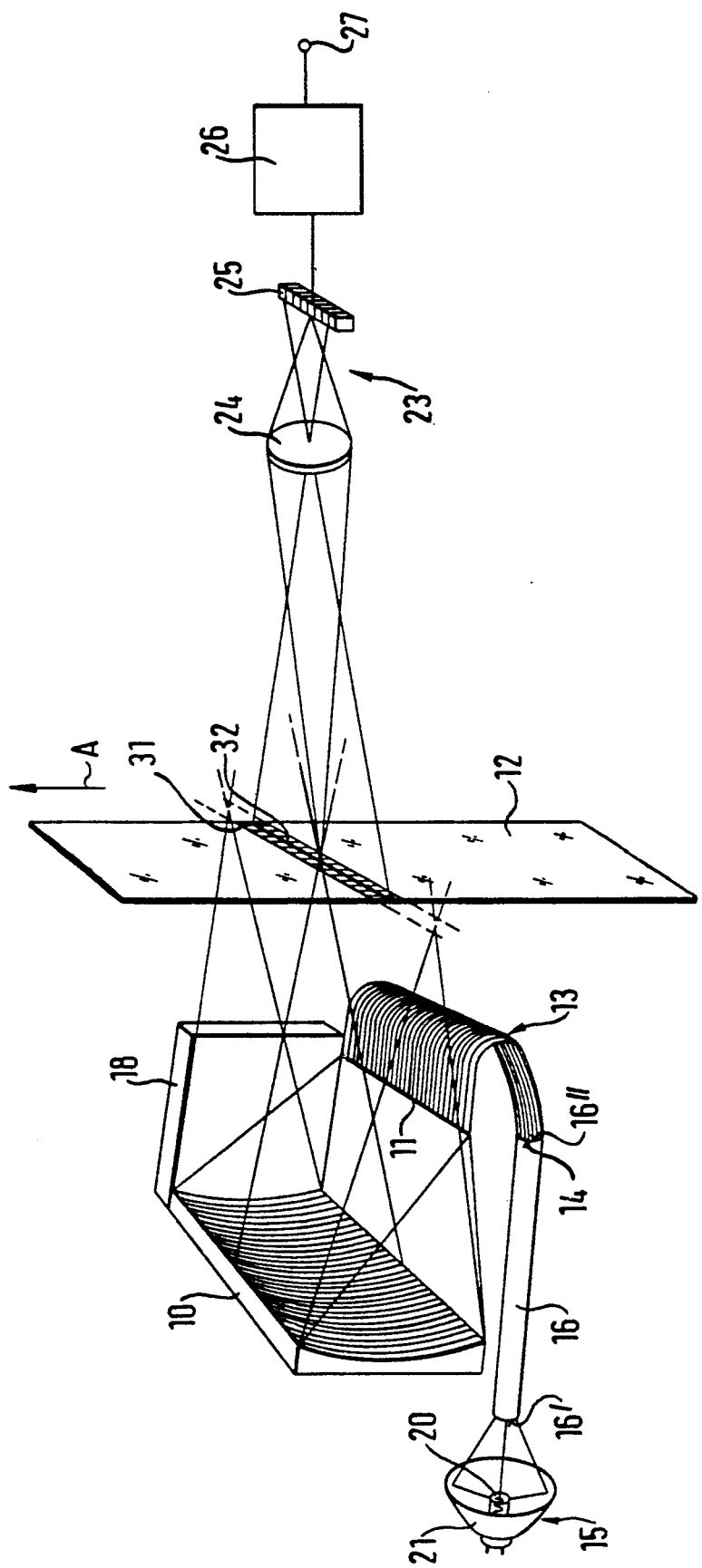

United States Patent [19]

Weber et al.

[11] Patent Number: 5,243,402
[45] Date of Patent: Sep. 7, 1993

[54] OPTICAL INSPECTION APPARATUS

[75] Inventors: Klaus Weber, Königsbronn; Wolfgang Siersch, München, both of Fed. Rep. of Germany

[73] Assignee: Erwin Sick GmbH Optik-Elektronik, Waldkirch, Fed. Rep. of Germany

[21] Appl. No.: 771,468

[22] Filed: Oct. 4, 1991

[30] Foreign Application Priority Data

Oct. 5, 1990 [DE] Fed. Rep. of Germany ....... 4031633

[51] Int. Cl.⁵ .............................................. G01N 21/84
[52] U.S. Cl. ..................................... 356/429; 356/430; 356/431; 250/572; 359/599; 359/853; 362/317; 362/325; 362/326
[58] Field of Search .................... 356/429, 430, 431; 250/572, 562; 359/599, 853, 855, 857, 859; 362/317, 325, 326, 334, 342

[56] References Cited

U.S. PATENT DOCUMENTS

| | | | |
|---|---|---|---|
| 3,645,601 | 2/1972 | Doctoroff et al. | 359/599 |
| 4,529,318 | 6/1985 | Curl | 356/430 |
| 4,810,095 | 3/1989 | Kawauchi et al. | 356/431 |
| 4,890,924 | 1/1990 | Beckstein | 356/429 |
| 4,900,153 | 2/1990 | Weber | 356/430 |
| 5,047,652 | 9/1991 | Lisnyansky et al. | 356/429 |

Primary Examiner—Vincent P. McGraw
Assistant Examiner—LaCharles Keesee
Attorney, Agent, or Firm—Townsend and Townsend Khourie and Crews

[57] ABSTRACT

The invention relates to an optical inspection apparatus comprising an illuminating means which has a linear light source (11) and a concave cylindrical mirror (10) which forms an image of the light source (11), with the cylindrical axis of the cylindrical mirror extending essentially parallel to the light source (11) in order to generate an illuminated strip (31) on a web (12) to be monitored, with the illuminated strip preferably extending over the entire width of the web (12). By means of an optical system (24) a light receiving means forms an image of an inspection line (32) extending on the material web (12) at the center of the illuminated strip (31) on a row-like photoreceiver arrangement (25), so that light emerging from the material web (12) is detected. The photoreceiver arrangement (25) is connected to an electronic processing circuit (26). The cylindrical mirror (10) which forms an image of the linear light source (11) has circumferentially extending grooves (17) arranged alongside one another in the cylindrical surface.

18 Claims, 3 Drawing Sheets

OPTICAL INSPECTION APPARATUS

The invention relates to an optical inspection apparatus comprising
an observing device which develops the image of an inspection line on a linear arrangement of photoreceivers of a CCD array,
an electronic evaluation means connected to the CCD array of the photoreceiver arrangement, and
an illuminating means in which a linear secondary light source is provided which extends beyond the length of the inspection line and is formed by the output side of a cross-section converter built up of light conducting fibers, the input side of which is matched to a light beam of preferably circular cross-section.

An optical web monitoring apparatus is known from DE-OS 35 34 019 the illuminating arrangement of which has a point light source which is imaged via a strip-like spherical concave mirror onto an aperture diaphragm in order to generate a secondary light source in this way. The secondary light source is imaged via a likewise strip-like spherical transmitting concave mirror, a deflecting mirror and a reflecting material web into the inlet pupil of a semiconductor row camera. In this arrangement a narrow illuminated strip is present on the material web which is observed by the row camera for the monitoring of the web.

This ensures that the photoreceiver arrangement of the row camera is illuminated with a high luminous intensity when the material web is regularly reflecting or clearly transparent. This arrangement is however unsuitable for diffusely reflecting or transmitting material.

In a known optical fault detector apparatus (DE-OS 30 13 244) a fluorescent lamp or the like is provided as a linear light source to generate an illuminated strip on an object which is essentially displaced perpendicular to the illuminated strip. The illuminated strip is observed by a Vidicon camera which serves as the photoreceiver arrangement and is connected to an electronic processing circuit. In this arrangement a cylindrical lens is provided between the objective of the Vidicon camera and the illuminated strip on the object to be investigated, with the cylindrical axis of the cylindrical lens extending essentially parallel to the illuminated strip.

It has however been shown that the luminous intensity (up to 2 sb) of fluorescent tubes is only rarely sufficient to enable troublefree optical fault monitoring or object recognition.

The German patent application P 37 24 294 describes an optical inspection apparatus in which one or more linear light sources are provided for generating an illuminated strip on a moved material web, with the light sources being imaged onto the material web by a cylindrical mirror the cylinder axis of which extends essentially parallel to the light sources. The illuminated strip on the material web is then imaged onto a row-like photoreceiver arrangement to which an electronic evaluation circuit is connected.

In this illuminating apparatus the light sources do not form an uninterrupted line. This has the consequence that a line of constant luminous intensity can admittedly be generated on the material web over the full inspection width, i.e. that all diffusely reflecting or transmitting materials can also be inspected, however with regularly reflecting or transmitting materials the inspection camera sees the interruptions in the linear arrangement of the light source.

The object of the present invention is now to provide an optical inspection apparatus of the initially named kind which is suitable both for the monitoring of diffusely reflecting or transmitting and also regularly reflecting or clear transmitting materials, with the inspection line on the web being illuminated both with a large aperture and a high luminous intensity, and with the background of this inspection line also appearing to the inspection camera as a continous uniformly bright strip.

This object is satisfied in accordance with the invention in that the linear secondary light source is imaged onto the inspection line by a cylindrical mirror which extends parallel to the secondary light source over its entire length in order to generate at the inspection line an illuminated strip of uniform high luminous intensity; and in that the cylindrical mirror has fine waves or grooves transverse to its axis. Through the inventive imaging of the linear secondary light source into the inspection line with the aid of a cylindrical mirror of the same length it is ensured that the image of this linear secondary light source appears uniformly narrow with sharp edges over a length which extends considerably beyond the length of the secondary light source and of the cylindrical mirror. This characteristic of the image formation by the cylindrical mirror is above all necessary when the later described build up of the illuminating means is to be realised for long inspection lines by arranging several linear secondary light sources and associated cylindrical mirrors in a row. A narrow illuminated strip with a uniformly high luminous intensity then arises over the whole length of the inspection line despite the overlapping of the images of the individual secondary light source sections.

When using cylindrical lenses or rods with circular cross-section with their comparatively shorter focal length in accordance with the prior art the overlapping faulty image sections of the neighbouring sections make themselves clearly noticable with such a row arrangement.

Through the finely waved or grooved formation of the cylindrical mirror as provided in accordance with the present invention which forms an image of the linear secondary light source it is ensured that the cylindrical mirror does not act in its longitudinal direction as a plane mirror, but rather the imaging of the linear light source onto the inspection line is smeared in this direction. During the inspection of non-scattering bare material surfaces it is precisely this smearing action of the grooved cylindrical mirror in the direction of the inspection line which is necessary, since the objective of the inspection camera, which is focussed onto the inspection line, sees a point of the secondary linear light source behind each point of this line—in transmission through the material web or in reflection at the surface of the material web and in reflection at the cylindrical mirror—as a luminous background, naturally with the lack of definition resulting from the distance. Each irregularity in the luminous intensity of the individual fiber ends in the direction of this line such as occur in particular with the plastic light guides of large cross-section, which are preferably used for large length of the inspection line because of the easier assembly, would allow the material web to appear irregularly bright along the inspection line in the absence of the smearing action of the grooves of the cylindrical mirror. Through the choice of the flank angle of the waves or grooves of the cylindrical mirror it is possible to smear this irregularity over a length of several centimeters without having to tolerate a large loss in the brightness of the image.

Thus one can generate not only a uniform and high luminous intensity on the material web or on the object to be monitored but rather background disturbances can also be avoided so that clearly transmitting or regularly reflecting materials can be monitored in troublefree manner.

With an advantageous embodiment of the invention provision is made that the width of the grooves amounts to 0.1 to 1 mm, preferably 0.5 mm. The groove structure then lies substantially below the diameter of the scattering circle on the mirror surface.

In a practical embodiment of the invention provision is made that the grooves of V-shaped or rounded cross-section are regularly arranged.

Another embodiment is characterised in that the grooves of differing width are irregularly arranged.

In order to simplify the manufacture of the inspection apparatus of the invention provision is made in a preferred further development for the light guiding fibers of the cross-section converter to consist of plastic and have a diameter which amounts to 0.5 mm to 1.5 mm, preferably to 1 mm, and for the linear light source to be formed in its width of only one or a few light fiber ends.

Thus, in the most favourable case, only 350 light guiding fibers are required to produce a light source of 350 mm. With a cross-section converter built up of light conducting glass fibers several thousand light conducting fibers would already be required for such a length since the light guiding fibers of glass may only have a relatively small thickness of approximately 50 μm in order to ensure corresponding bending elasticity of the fibers. The processing of several thousand individual light guiding fibers is however complicated and thus costly, in particular since the light entry and or exit surfaces of the light fibers of glass require complicated and costly finishing in order to ensure the required optical quality.

In order to achieve a light distribution to the individual light outlet surfaces of the cross-section converter which is as homogeneous as possible provision is made in accordance with a preferred embodiment of the invention for the light entry surface of the cross-section converter to be connected to the light exit surface of a light conducting rod operating as a homogeniser, with the light inlet surface of the light conducting rod being illuminated by the primary light source.

To avoid unnecessary light losses at the transition from the light conducting rod acting as a homogeniser to the cross-section converter the light outlet surface of the light conducting rod is bonded or cemented to the light inlet surface of the cross-section converter, with the diameter of the light conducting rod corresponding to the diameter of the light inlet surface of the cross-section converter.

In a particularly preferred further development of the invention provision is made that the light entry surface of the light conducting rod is mat. In this way a homogenisation is achieved of the light radiated by the individual fiber ends over the whole angular range of their useful aperture. For the building up of linear light sources which are as long as possible provision is made in accordance with a further development of the invention that the first and last point-like light source of the linear light source are freely arranged at their outwardly disposed ends in the longitudinal direction of the linear light source so that two or more linear light sources can be arranged in a row in a longitudinal direction without gaps.

In this way it is ensured that an optical inspection apparatus in accordance with the invention can be assembled the light source of which be assembled from modules of individual compact linear light sources which preferably each have their own primary light source and a cross-section converter, so that in particular material webs with a width of for example 2 m can be monitored.

In a practical embodiment in accordance with the invention provision is made that with a linear light source consisting of two or more linear individual light sources arranged in a row a cylindrical mirror arrangement is provided which is put together of cylindrical mirrors of the same construction which are arranged in a row without gaps in the same manner, with the length of each cylindrical mirror respectively corresponding to the length of the oppositely disposed individual linear light source.

In this way it is ensured that the described illuminating means which are built up as modules comprising a linear light source and an associated cylindrical mirror can be arranged directly alongside one another, so that the length of the illuminated strip generated on the material web or on the object to be monitored can be straightforwardly enlarged depending on the requirements.

In order to maintain the homogeneous distribution of the luminous intensity of the illuminating strip also at the two ends of the inspection line detected by the camera, and to simultaneously allow the background seen by the camera at the two ends of the inspection line to appear without a drop of brightness it is necessary to select the total length of the illuminating arrangement to be larger than the desired total length of the inspection line. The required additional length depends on the image angle of the camera, on the aperture angle of the illuminating individual light fibers in the direction of the inspection line and on the spacing of the cylindrical mirror from the light line and the illuminating strip.

In an advantageous further development of the invention provision is made for a plane mirror to be mounted perpendicular to the cylinder axis at the free ends of the cylinder mirror arrangement in order in this way to bring about a virtual extension of the cylindrical mirror and the light line and thus to shorten the required real extension of the two.

For the realisation of a symmetical dark field illumination provision is made for a stop to be arranged on a central strip of the cylindrical mirror extending parallel to the cylinder axis.

Figure 2:
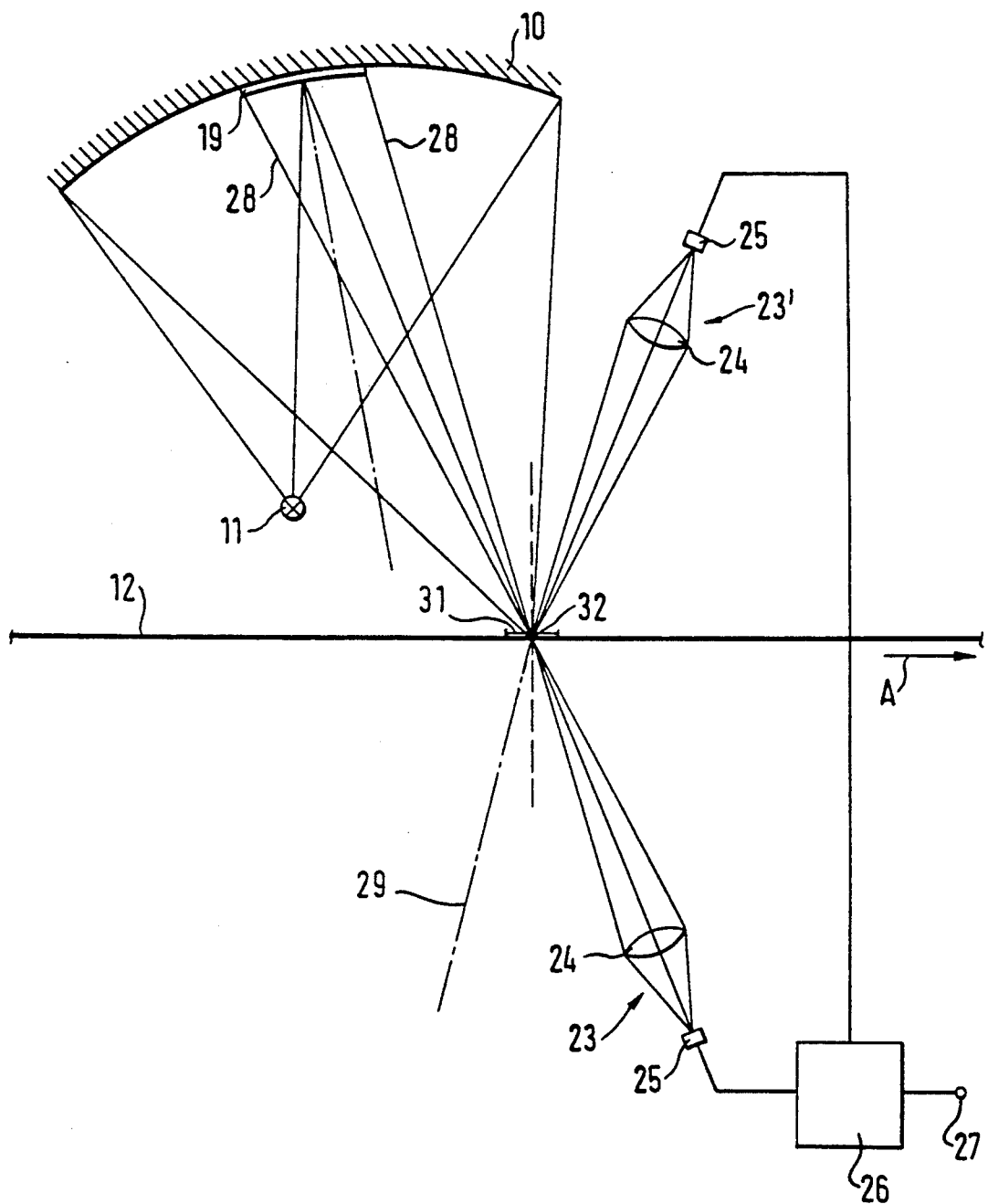
Figure 5:
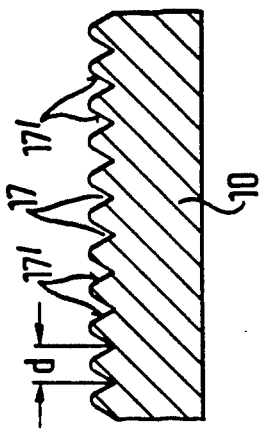
Figure 3:
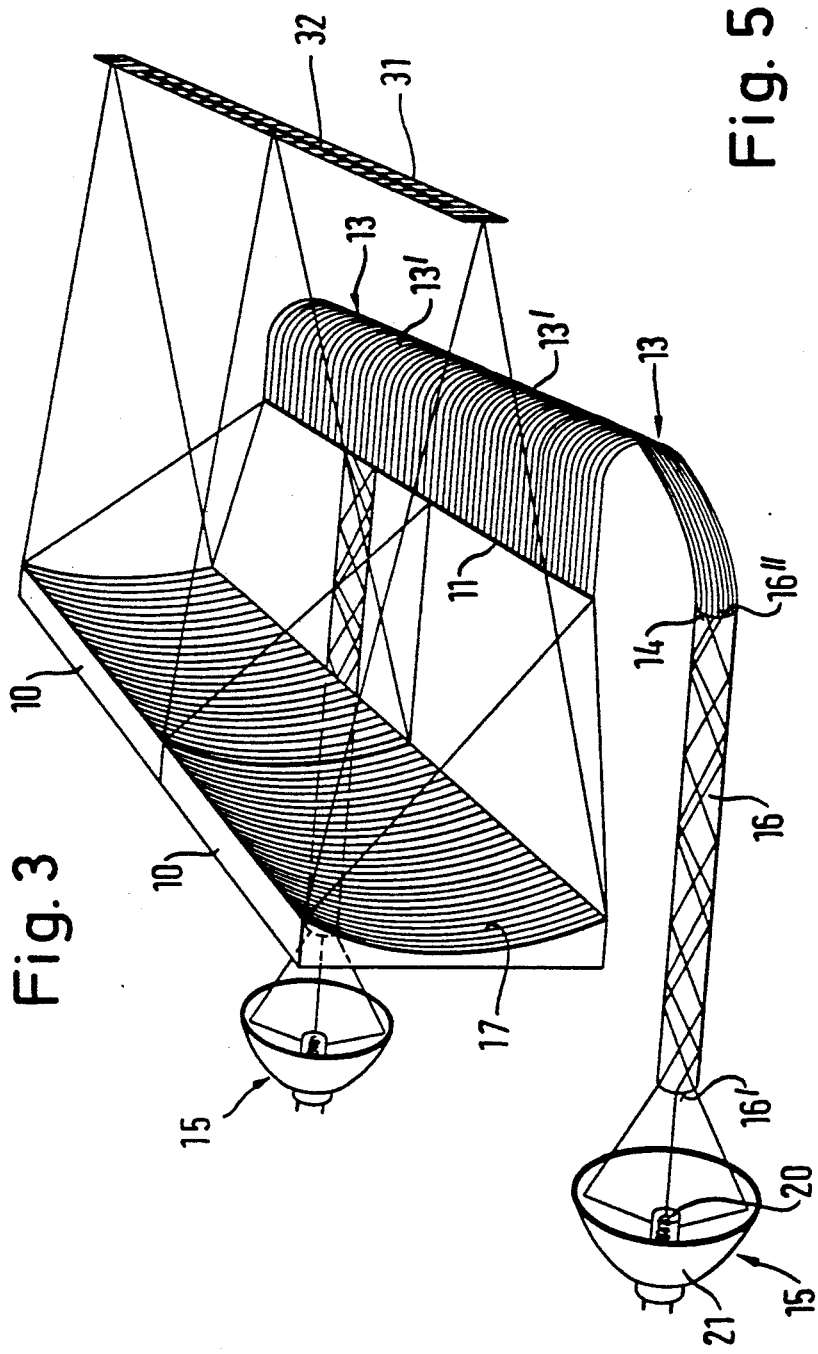
Figure 4:
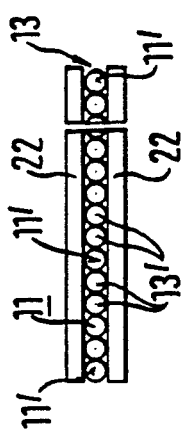

The invention will now be explained in more detail in the following with reference to the drawings in which are shown:

FIG. 1 a schematic view of an optical inspection apparatus operating in transmission, FIG. 2 a schematic section through an optical inspection apparatus parallel to the direction of advance of a material web, FIG. 3 a schematic perspective illustration of an illuminating means put together of modules and with an increased length for an optical monitoring apparatus in accordance with FIG. 1 or 2, FIG. 4 a partial plan view onto the light exit surfaces of a linear light source of the illuminating means of FIG. 3, and FIG. 5 a part section through a cylindrical mirror of the illuminating means of FIG. 3 parallel to the longitudinal cylinder axis.

In the various figures of the drawing components which correspond to one another are designated with the same reference numerals.

In FIG. 1 the optical inspection apparatus has a compact primary light source 15 which has an incandescent lamp 20 with a reflector 21 which concentrates the light emerging from the incandescent lamp onto a mat light entry surface 16' of a light conducting rod 16. A light exit surface 16" of the light conducting rod 16 is cemented (bonded) to a light entry surface 14 of a cross-section converter 13 which is built up of individual light conducting fibers 13' as can be seen particularly well in FIG. 3.

The light conducting rod 16 acts as a homogeniser for the luminous intensity generated by the light source 15 at its light entry surface 16' because the light beams which are incident at different angles, of which only three are shown in the drawing, are reflected at different angles in the light conducting rod, as indicated in FIG. 3. In this way a homogenous distribution of the luminous intensity results in the light exit surface 16" of the light conducting rod 16 which has the consequence that all the light conducting fibers 13' of the cross-section converter 13 are illuminated with the same luminous intensity at their light entry surfaces.

The light conducting fibers 13' of the cross-section converter 13, which are preferably manufactured of plastic and have a diameter of about 1 mm are combined into a round bundle at their ends associated with the light entry surface 14 of the cross-section converter 13, with the diameter of this round bundle being substantially the same as the diameter of the light conducting rod 16. At their other ends the light exit surfaces 11' of the light conducting fibers are arranged in a row closely alongside one another, as shown in FIG. 4, so that they form the individual elements of a linear secondary light source 11. The cross-section converter 13 is in this arrangement for example built up of 350 individual light conducting fibers 13 so that the linear light source 11 formed by the light exist surfaces 11' has a length of 350 mm.

In order to obtain a stable linear light source 11 the light conducting fibers 13' as shown in FIG. 4 are bonded at their ends to strips 22 which ensure the straight build up of the linear light source 11. In this arrangement the first and last light conducting fibers are so arranged that they are exposed towards the outside as seen in the longitudinal direction of the light source 11 so that two or more cross-sectional converters 13 can be arranged in a row without gaps in order to form a linear light source 11 of enlarged length, as shown in FIG. 3.

In this way it is possible to build up linear light sources with a lenght of 2 m or more, depending on the width of the web to be monitored.

The light exit surface of the cross-sectional converter 13 which forms the secondary linear light source 11 is imaged via a concave cylindrical mirror 10 onto a material web 12 for example, whereby an illuminating strip 31 is generated on the web 12. The web 12 which is shown in FIG. 1 as consisting of transparent material is advanced in the direction of the arrow A. At the axial ends of the cylindrical mirror there is in each case provided a plane mirror 18 perpendicular to its cylinder axis and perpendicular to the linear light source 11, with only one of the two plane mirrors 18 being schematically illustrated in FIG. 1. In this arrangement the plane mirror 18 must extend at least from the cylindrical mirror 10 up to the linear light source 11. In this way a virtual extension of the cylinder mirror 10 and of the linear secondary light source 11 is brought about.

Behind the web 12 of transparent material, as seen from the illuminating means, there is arranged a row camera 23 the objective 24 of which forms an image of the inspection line 32 which extends at the center of the illuminated strip 31 onto a linear photoreceiver arrangement, for example a diode row 25. An electronic processing circuit 26 is connected to the diode row 25 and has an output 27 at which faults or image signals are present.

As shown in FIG. 2 the inspection apparatus can have a second row camera 23' in place of or in addition to the row camera 23 which lies behind the material web 12 and operates in transmission, with the second row camera 23' lying on the same side of the material web as the illuminating means and operating in reflection.

The illuminating means shown in FIG. 2 comprising the secondary linear light source 11 and the cylindrical mirror 10 is provided with a stop 19 to realise a dark field illuminating system and the stop 19 covers over a central strip of the cylindrical mirror extending parallel to the cylinder axis, with the angular size of the covered over strip of the cylindrical mirror perpendicular to the linear light source 11 as viewed from the illuminates strip 31 corresponding to the entry aperture of the objective 24 of the row camera 23 as is illustrated by the extended marginal rays 28 for the imaging of the inspection line 32 by the objective 24.

A dark field illumination can also be realised in that the optical axis of the objective of the row camera 23' is pivoted out of the region of the angle of illumination of the cylindrical mirror, for example into the direction 29.

As illustrated in FIGS. 3 and 5 the concave cylindrical mirror 10 has a plurality of grooves 17 the flanks 17' of which are regularly reflecting. A cylindrical mirror of this kind can be manufactured by milling with a so-called one tooth and by subsequent polishing in the direction of milling, i.e. in the circumferential direction of the cylindrical mirror 10. The cylindrical mirror 10 thus has a finely corrugated or waved surface with a washboard structure. The shape of the grooves 17 can be V-shaped or U-shaped. The grooves 17 have a spacing d which is matched to the size of the individual light sources, that is to say to the light exit surfaces 11' of the light conducting fibers 13' of the cross-section converter 13 and to the object side aperture of the objective 24, with a spacing of 0.5 mm preferably being selected which thereby corresponds to half the diameter of the light exit surfaces 11' of the light conducting fibers 13, with a plurality of grooves 17 lying in the scattering circle given by the object side aperture of the objective.

In the plane perpendicular to the linear light source 11 the cylindrical mirror 10 with the described finely corrugated washboard structure thus forms an image in a regular manner of each light exit surface 11' serving as an essentially point-like individual light source of the secondary linear light source 11. In contrast, parallel to the light source Il the cylindrical mirror 10 generates for each light exit surface 11' a plurality of dash-like images in the illuminating strip 31 since it has a scattering action parallel to the light source 11 due to its washboard-like structure. The individual dash-like images of the individual light sources 11' are superimposed in the illuminating strip 31 so that the latter has a homongeous distribution of the luminous intensity independent of the structure of the linear light source. The plane mirrors 18 provided at the ends of the cylindrical mirror 10 ensure that even for reduced additional length of the cylindrical mirror 10 and the linear light source 11 there is still no drop-off in the luminous intensity in the illuminated strip 31 at the two ends of the inspection line 32.

The row camera 23 which observes the inspection line 32 extending at the center of the illuminated strip 31 in reflection or transmission now sees, as a consequence of the finely corrugated washboard structure of the cylindrical mirror 10 a structureless linear light source 11 in the background of the illuminating strip 31 so that the linear light source 11 also forms a uniform band in the pupil space of the row camera 23 as a result of the described cylindrical mirror 10 although it is structured as a consequence of the row of light exit surfaces 11' of the light conducting fibers 13'.

We claim:

1. Optical inspection apparatus comprising:
   an observing device which develops the image of an inspection line on a linear arrangement of photoreceivers of a CCD array,
   an electronic evaluation means connected to the CCD array of the photoreceiver arrangement, and
   an illuminating means in which a linear secondary light source is provided which extends beyond the length of the inspection line and is formed by the output side of a cross-section converter built up of light conducting fibers and having an input side which is matched to a light beam of circular cross-section,
   characterized in that
   the linear secondary light source (11) is imaged onto the inspection line (32) by a cylindrical mirror (10) for reflecting all light received by it from the secondary light source and which extends parallel to the secondary light source (11) over its entire length in order to generate at the inspection line 32 an illuminated strip of uniform high luminous intensity; and
   in that the cylindrical mirror (10) has grooves arranged transverse to its axis, which are uniformly spaced, and have one of a V-shaped and a rounded cross-section to effect a substantially random reflection of the light received by the mirror.

2. Inspection apparatus in accordance with claim 1, characterized in that the width of the grooves (17) amounts to 0.1 to 1 mm.

3. Inspection apparatus in accordance with claim 1, characterised in that the light guiding fibers (13') of the cross-section converter (13) consist of plastic and have a diameter which amounts to 0.5 mm to 1.5 mm, and in that the linear light source (11) is formed in its width of one or only a few light conductor ends.

4. Inspection apparatus in accordance with claim 3, characterised in that the light entry surface (14) of the cross-section converter (14) is connected with the light exit surface (16'') of a light conducting rod (16) acting as a homogeniser, the light entry surface (16') of which is illuminated by the primary light source (15).

5. Inspection apparatus in accordance with claim 4, characterised in that the light exit surface (16'') of the light conducting rod (16) is cemented to the light entry surface (14) of the cross-section converter (13), with the diameter of the light conducting rod (16) corresponding to the diameter of the light entry surface (14) of the cross-section converter (13).

6. Inspection apparatus in accordance with claim 5, characterised in that the light entry surface (16') of the light conducting rod (16) is a mat surface.

7. Inspection apparatus in accordance with claim 1, characterised in that the first and last light fiber ends (11') of the linear light source (11) as seen in the longitudinal direction of the linear secondary light source (11) are freely arranged at their outwardly disposed ends so that two or more linear light sources (11) can be arranged in series in their longitudinal direction without gaps.

8. Inspection apparatus in accordance with claim 1, characterised in that, with a linear light source which comprises two or more linear individual light sources (11) arranged in a row, a cylindrical mirror arrangement is provided which is comprised of cylindrical mirrors (10) of the same construction which are arranged in a row without gaps, with the length of the cylindrical mirrors respectively corresponding to the length of the oppositely disposed individual linear light source (11).

9. Inspection apparatus in accordance with claim 1, characterised in that a plane mirror (18) is provided at each of the free ends of the cylindrical mirror arrangement, perpendicular to the cylindrical axis in order to so bring about a virtual extension of the arrangement comprising of one or more cylindrical mirrors (10) and light sources (11).

10. Inspection apparatus in accordance with claim 1, characterised in that an aperture stop (19) is arranged on a central strip of the cylindrical mirror (10) extending parallel to the cylindrical axis in order to realise a symmetrical dark field illumination system.

11. Optical inspection apparatus comprising:
    an observing device which develops the image of an inspection line on a linear arrangement of photoreceivers of a CCD array,
    an electronic evaluation means connected to the CCD array of the photoreceiver arrangement, and
    illuminating means in which a linear secondary light source is provided which extends beyond the length of the inspection line and is formed by the output side of a cross-section converter built up of light conducting fibers and having an input side which is matched to a light beam of circular cross-section,
    characterized in that
    the linear secondary light source is imaged onto the inspection line by a cylindrical mirror which extends parallel to the secondary light source over its entire length in order to generate at the inspection line an illuminated strip of uniform high luminous intensity; and
    in that the cylindrical mirror has grooves transverse to its axis of a width between 0.1 and 1 mm.

12. Optical inspection apparatus comprising:
    an observing device which develops the image of an inspection line on a linear arrangement of photoreceivers of a CCD array,
    an electronic evaluation means connected to the CCD array of the photoreceiver arrangement, and
    illuminating means in which a linear secondary light source is provided which extends beyond the length of the inspection line and is formed by the output side of a cross-section converter built up of light conducting fibers and having an input side which is matched to a light beam of circular cross-section, characterized in that the light conducting fibers of the cross-section converter are constructed of plastic and have a diameter of between 0.5 mm to 1.5 mm;

the linear light source has a width defined by one or only a few light conductor ends;

the linear secondary light source is imaged onto the inspection line by a cylindrical mirror which extends parallel to the secondary light source over its entire length in order to generate at the inspection line an illuminated strip of uniform high luminous intensity; and in that the cylindrical mirror has fine grooves oriented transverse to its axis.

13. Optical inspection apparatus comprising:

an observing device which develops the image of an inspection line on a linear arrangement of photoreceivers of a CCD array, an electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that the linear secondary light source is imaged onto the inspection line by a cylindrical mirror which extends parallel to the secondary light source over its entire length in order to generate at the inspection line an illuminated strip of uniform high luminous intensity;

a light entry surface of the cross-section converter is connected with a light exit surface of a light conducting rod acting as a homogenizer, a light entry surface of the rod being illuminated by the primary light source;

a light exit surface of the light conducting rod is cemented to the light entry surface of the cross-section converter, with the diameter of the light conducting rod corresponding to the diameter of the light entry surface of the cross-section converter; and in that the cylindrical mirror has grooves transverse to its axis.

14. Optical inspection apparatus comprising:

an observing device which develops the image of an inspection line on a linear arrangement of photoreceivers of a CCD array, electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that the linear secondary light source is imaged onto the inspection line by a cylindrical mirror which extends parallel to the secondary light source over its entire length in order to generate at the inspection line an illuminated strip of uniform high luminous intensity;

a light entry surface of the cross-section converter is connected with a light exit surface of a light conducting rod acting as a homogenizer, a light entry surface of the rod being illuminated by the primary light source and defined by a mat surface; and in that the cylindrical mirror has fine grooves oriented transverse to its axis.

15. Optical inspection apparatus comprising:

an observing device which develops the image of an inspection line on a linear arrangement of photoreceivers of a CCD array, electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that the linear secondary light source is imaged onto the inspection line by a cylindrical mirror which extends parallel to the secondary light source over its entire length in order to generate at the inspection line an illuminated strip of uniform high luminous intensity;

ends of first and last light fibers of the linear light source as seen in a longitudinal direction of the linear secondary light source are freely arranged at their outwardly disposed ends so that two or more linear light sources can be arranged in series in their longitudinal direction without the formation of gaps between them; and in that the cylindrical mirror has fine waves or grooves transverse to its axis.

16. Optical inspection apparatus comprising:

an observing device which develops the image of an inspection line on a linear arrangement of photoreceivers of a CCD array, electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that at least two linear secondary light sources are imaged onto the inspection line by a cylindrical mirror for each which extends parallel to the secondary light source over its entire length in order to generate at the inspection line an illuminated strip of uniform high luminous intensity;

the cylindrical mirrors are arranged in a row without gaps between them and have a length corresponding to the length of the linear light sources associated with them; and in that the cylindrical mirror has fine waves or grooves transverse to its axis.

17. Optical inspection apparatus comprising:

an observing device which develops the image of an inspection line on a linear arrangement of photoreceivers of a CCD array, electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that the linear secondary light source is imaged onto the inspection line by a cylindrical mirror which extends parallel to the secondary light source over its entire length in order to generate at the inspection line an illuminated strip of uniform high luminous intensity;

in that the cylindrical mirror has fine waves or grooves transverse to its axis; and a plane mirror is provided at each end of the cylindrical mirror and is perpendicular to an axis of the cylindrical mirror to effect a virtual extension comprising at least one cylindrical mirror and light source.

18. Optical inspection apparatus comprising:

an observing device which develops the image of an inspection line on a linear arrangement of photoreceivers of a CCD array, electronic evaluation means connected to the CCD array of the photoreceiver arrangement, and illuminating means in which a linear secondary light source is provided which extends beyond the length of the inspection line and is formed by the output side of a cross-section converter built up of light conducting fibers and having an input side which is matched to a light beam of circular cross-section, characterized in that the linear secondary light source is imaged onto the inspection line by a cylindrical mirror which extends parallel to the secondary light source over its entire length in order to generate at the inspection line an illuminated strip of uniform high luminous intensity;

in that the cylindrical mirror has fine waves or grooves transverse to its axis; and an aperture stop is arranged on a central strip of the cylindrical mirror extending parallel to an axis of the cylindrical mirror for realizing a symmetrical dark field illumination system.

* * * * *